US010463381B2

(12) United States Patent
Voic et al.

(10) Patent No.: US 10,463,381 B2
(45) Date of Patent: Nov. 5, 2019

(54) ULTRASONIC SURGICAL PROBE, ASSEMBLY, AND RELATED METHOD

(71) Applicant: MISONIX, INCORPORATED, Farmingdale, NY (US)

(72) Inventors: Dan Voic, Cedar Grove, NJ (US); Scott Isola, Deer Park, NY (US); Paul Mikus, Trabuco Canyon, CA (US)

(73) Assignee: MISONIX, INC., Farmingdale, NY (US)

( * ) Notice: Subject to any disclaimer, the term of this patent is extended or adjusted under 35 U.S.C. 154(b) by 425 days.

(21) Appl. No.: 15/221,271

(22) Filed: Jul. 27, 2016

(65) Prior Publication Data

US 2018/0028207 A1 Feb. 1, 2018

(51) Int. Cl.
*A61B 17/22* (2006.01)
*A61B 17/32* (2006.01)
*A61N 7/00* (2006.01)

(52) U.S. Cl.
CPC .......... *A61B 17/22004* (2013.01); *A61B 17/320068* (2013.01); *A61B 2017/320008* (2013.01); *A61B 2017/320072* (2013.01); *A61B 2017/320084* (2013.01); *A61B 2217/005* (2013.01); *A61N 2007/0017* (2013.01)

(58) Field of Classification Search
CPC .................. A61B 17/22004; A61B 17/320068
See application file for complete search history.

(56) References Cited

U.S. PATENT DOCUMENTS

| 4,425,115 | A | * | 1/1984 | Wuchinich | ....... A61B 17/22004 310/26 |
| 4,988,334 | A | * | 1/1991 | Hornlein | ........ A61B 17/320068 601/2 |
| 6,799,729 | B1 | * | 10/2004 | Voic | ......................... B08B 3/02 239/102.2 |
| D627,463 | S | * | 11/2010 | Voic | ............................ D24/144 |
| 2010/0076349 | A1 | * | 3/2010 | Babaev | .................... A61N 7/02 601/2 |
| 2016/0128707 | A1 | | 5/2016 | Mikus et al. | |

OTHER PUBLICATIONS

Misonix, Inc. "Sonicone Plus. Ultrasonic Debridement System" Brochure 2013 pp. 1-4.

* cited by examiner

*Primary Examiner* — Richard G Louis
(74) *Attorney, Agent, or Firm* — R. Neil Sudol; Henry D. Coleman

(57) ABSTRACT

An ultrasonic surgical probe has an elongate shaft and a probe head that is enlarged to extend laterally or transversely in two opposed directions relative to the shaft The head is formed with a recess or cavity facing laterally in a third direction relative to the shaft and the axis. Where the head lies in a plane, owing to its lateral enlargement or extension, the recess or cavity faces in a direction perpendicular to that plane. The recess or cavity is defined in part by an inclined floor or base surface contiguous at a proximal end with the shaft. The recess or cavity is defined in part by a peripheral wall extending only partway around the recess or cavity, along a distal side and two lateral sides thereof. The cavity or recess is closed on a proximal side by the inclined surface and the shaft.

17 Claims, 8 Drawing Sheets

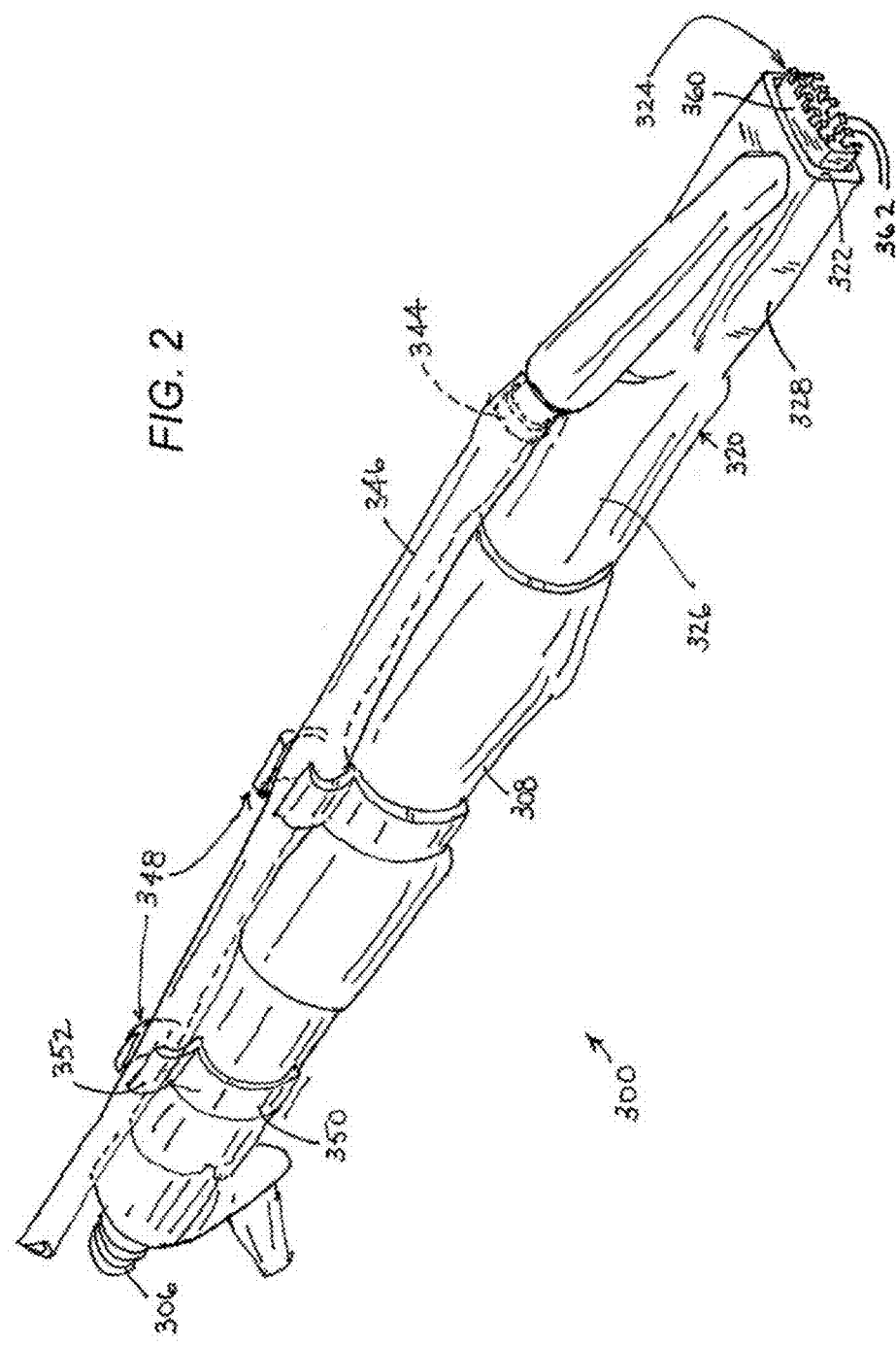

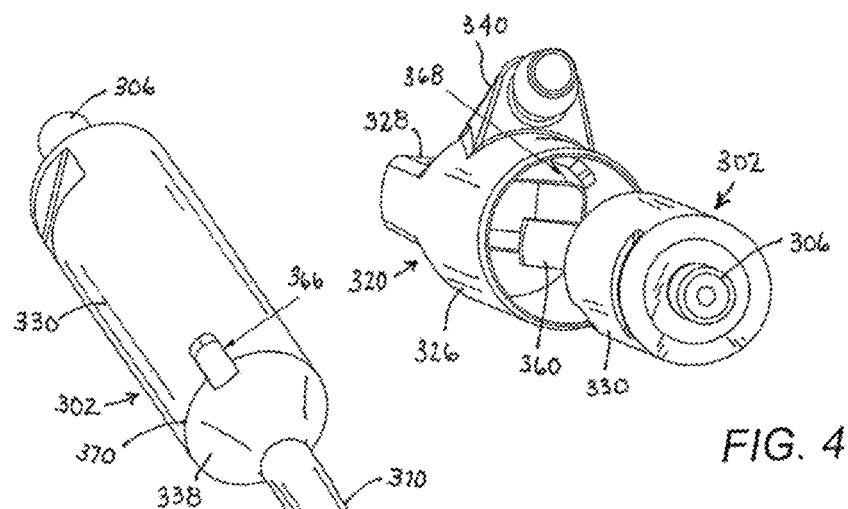
FIG. 4
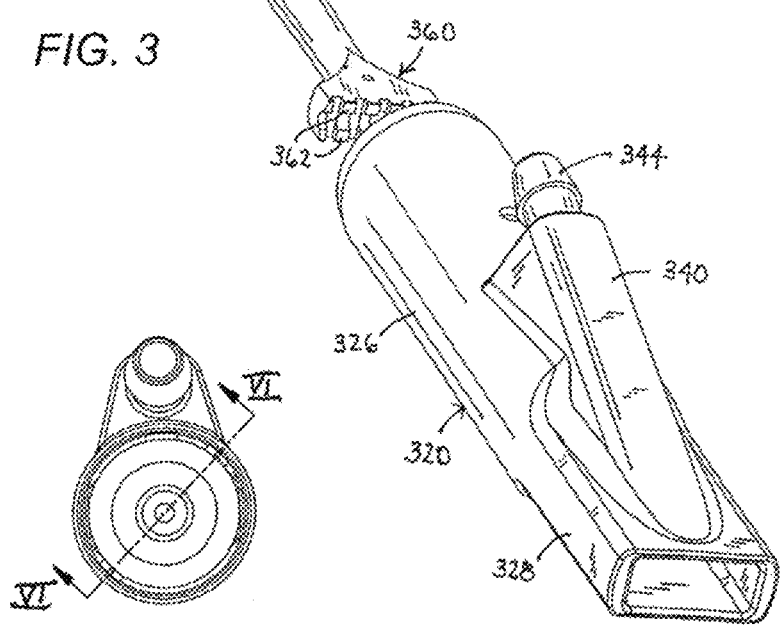
FIG. 3
FIG. 5

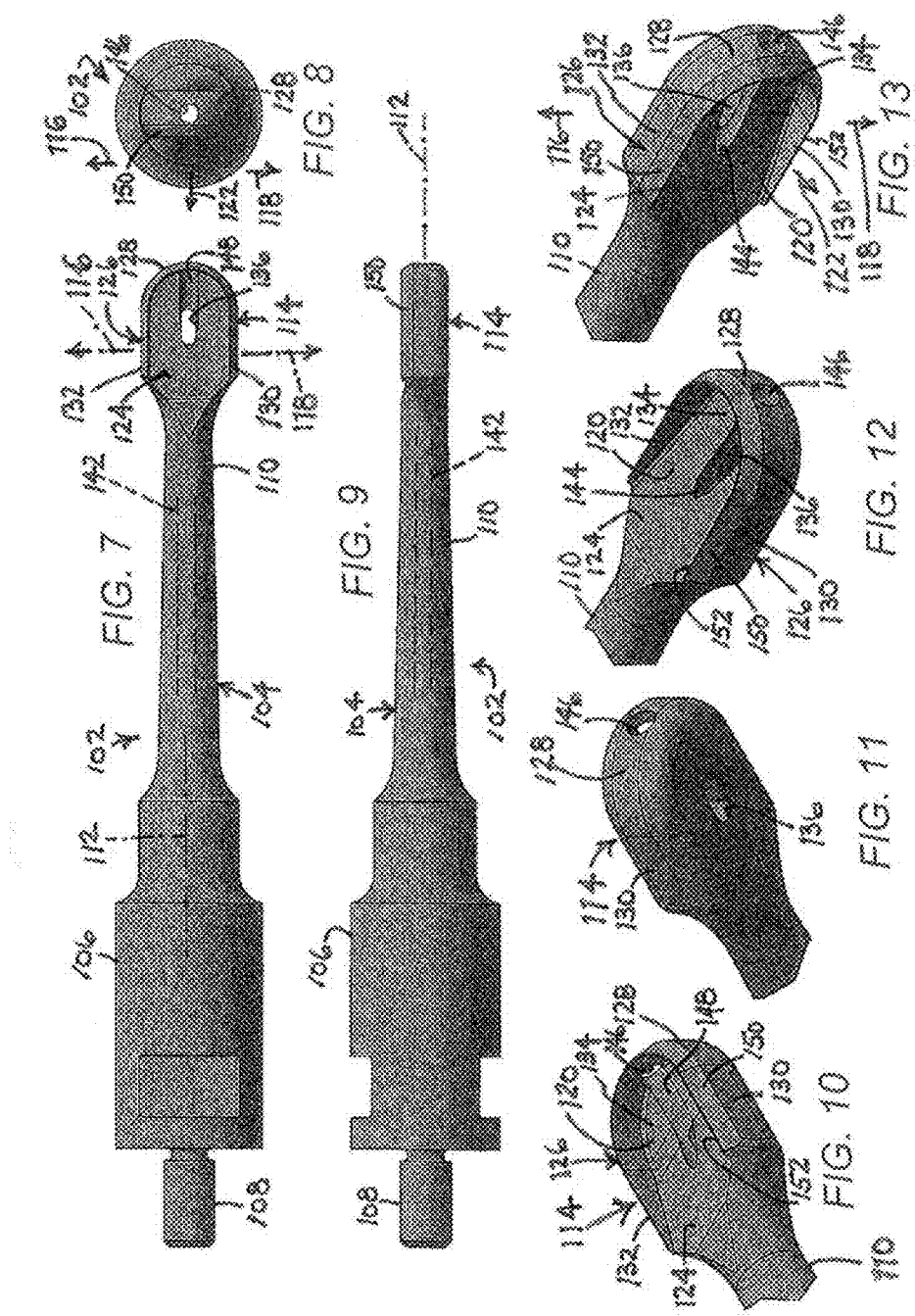

ULTRASONIC SURGICAL PROBE, ASSEMBLY, AND RELATED METHOD

BACKGROUND OF THE INVENTION

This invention relates to an ultrasonic surgical probe. This invention also relates to an assembly of a probe and a sheath. The invention additionally relates to an associated method for operating on a surgical site, exemplarily to reduce biofilm on a wound site particularly a wound site that is being debrided to remove necrotic tissue.

Chronic wound infection represents a significant healthcare problem worldwide. Often the end objective of wound healing is the objective for new therapeutic options. Yet chronic wounds compromise a number of different and complex conditions that each interferes with the healing process. For example, a chronic wound can comprise necrotic tissue in need of debridement, bacterial infection in need of antimicrobial agents and compromised vasculature that impedes the normal healing process.

One element of the chronic wound infection condition that impedes healing is the formation of biofilm. Biofilm is the result of planktonic bacteria forming together and secreting exopolysaccharide (EPS) to adhere and protect the colonizing community. At the height of formation, EPS can make up between 75-90% of the total biofilm composition (Regt). Biofilm inhibits healing by creating an optimal condition for bacteria to grow, while simultaneously preventing antimicrobial agents from direct access to bacteria.

Methods to remove biofilm include ultrasonic debridement, topical antimicrobials, suction, and surface cleansing. Each of these methods alone treat an aspect of biofilm. For example, ultrasonic debridement of wounds has proven to be the most effective mechanism in disrupting and debulking a majority of the biofilm formation. Yet even in this preferred method, biofilm debris can be left behind to propagate. Suction alone has not proven to be effective in removing biofilm, and can potentially interfere with the operation of other methods like ultrasonic debridement if applied simultaneously.

U.S. Pat. No. 7,608,054 to Soring et al. describes a medical treatment apparatus that combines an ultrasound sonotrode with a suction sheath. The fixed position between the tip of the suction and the tip of the sonotrode only allows for one simultaneous operation. In particular this approach is limited due to the potential interference of the suction tip during the ultrasonic debridement operation.

U.S. Pat. No. 7,522,955 B2 to Rontal et al. describes a method and apparatus for ultrasonic cleaning of biofilm coated surfaces for sinus cavities within a human head. The method describes an ultrasonic application in combination with irrigation and suction that is designed to not remove any of the surrounding underlying tissue. This differs significantly from an ultrasonic debridement of a wound bed, which requires the removal of tissue in combination with biofilm. Thus the ultrasonic probe needs to operate in a cavitation mode at the surface of a wound, causing destruction of the biofilm.

Methods of mechanical removal of biofilm in wounds alone have proven to be inadequate. What does not exist and what would be beneficial to the market is an ultrasonic probe or instrument assembly which permits implementation of an improved method to remove biofilm and prevent it from reforming in order to allow wounds to heal.

OBJECTS OF THE INVENTION

It is an object of the present invention to provide an improved ultrasonic probe and/or instrument assembly.

A more particular object of the present invention is to provide such an ultrasonic probe and/or instrument assembly that permits execution of an improved method to inhibit biofilm formation in order to allow wounds to heal more expeditiously.

A related object of the present invention is to provide an improved method for wound debridement or biofilm removal.

Although every feature of the invention is attained in at least one embodiment of the invention, there is not necessarily any one embodiment that achieves all of the objects of the invention.

SUMMARY OF THE INVENTION

An ultrasonic surgical probe comprises, in accordance with the present invention, an elongate shaft having a distal end portion with a longitudinal axis and a probe head that is enlarged to extend laterally or transversely in two opposed directions relative to the shaft and the axis. The head is formed with a recess or cavity facing laterally in a third direction relative to the shaft and the axis. Where the head is conceptualized as lying in a plane, owing to its lateral enlargement or extension, the recess or cavity faces in a direction perpendicular to that plane. The recess or cavity is defined in part by an inclined floor or base surface contiguous at a proximal end with the shaft. The recess or cavity is defined in part by a peripheral wall extending only partway around the recess or cavity, along a distal side and two lateral sides thereof. The cavity or recess is closed on a proximal side by the inclined surface and the shaft.

Pursuant to further features of the present invention, the recess or cavity is further defined by an additional floor or base surface located distally of the inclined floor or base surface. The additional floor or base surface is planar or flat and oriented parallel to the axis. Preferably, the inclined floor or base surface is also planar or flat.

The distal, additional floor or base surface and the proximal, inclined floor or base surface are preferably adjacent and contiguous with one another.

Pursuant to further features of the present invention, the probe head is provided in at least one of the inclined floor or base surface and the additional floor or base surface with at least one first opening spaced from the peripheral wall. The opening permits the egress of pressurized fluid from the recess or cavity into a space surrounding the probe head, exemplarily into a channel in a sheath that surrounds the probe. The pressurized fluid is liquid irrigant which serves to cool the surfaces of the probe head, particularly including those surfaces that contact tissue during an ultrasonic debridement or biofilm removal procedure. The pressurized fluid is fed into the recess or cavity via an axial channel or through bore in the probe shaft. The channel or through bore has an outlet port at least partially in or at the inclined floor or base surface.

Preferably, the probe head is provided with a second opening or through hole in the peripheral wall at a distal end of the probe head. A groove may be formed in the floor of the recess or cavity, with the first opening or through hole located in the groove, the groove extending to the second opening or through hole.

The groove may be formed during manufacture during the drilling of a probe blank to form the channel in the shaft. The inclined floor or base surface and the additional floor or base surface are subsequently formed by machining one side of the head of the blank. This machining opens a side of the channel in the head and thereby generates the groove.

Pursuant to other features of the present invention, the peripheral wall of the recess or cavity includes a cylindrical section on the distal side of the recess or cavity and further includes two linear sections on the lateral sides of the recess or cavity. The peripheral wall thus has a U-shaped plan or configuration.

In accordance with another feature of the present invention, the peripheral wall is provided with a beveled surface, on a side of the peripheral wall opposite the recess or cavity, and has a flat terminal edge in a plane parallel to the axis. The flat terminal edge or rim enables the peripheral wall to transmit ultrasonic vibratory energy into the tissues at a surgical site during a debridement or biofilm elimination procedure.

It is to be noted that the multiple openings in the head, one in the floor and one in on the distal portion of the peripheral wall, facilitate the flow of liquid irrigant in part to optimize cooling of the peripheral wall and the tissues at the surgical site, thus reducing if not eliminating damage to the healthy tissue which remains after the debridement procedure. The floor geometry of the recess or cavity in the probe head acts to deflect and guide removed tissue fragments from the recess or cavity, thereby inhibiting if not completely preventing the clogging of the openings in the probe head. In addition, the flow of liquid irrigant or coolant into the recess or cavity through the channel or bore in the shaft and out through the openings in the floor and the peripheral wall help move the separated tissue fragments along the floor surfaces and out of the recess or cavity. The floor structure of the recess or cavity assists in maintaining desired cooling for longer periods of time.

A surgical instrument assembly comprises, in accordance with the present invention, an ultrasonic probe having an operative tip, an electromechanical transducer operatively connected to the probe for generating an ultrasonic standing wave in the probe, and at least one sheath or sleeve disposed about the probe and defining at least a first suction port at a distal end of the probe, proximate the operative tip thereof, and a second suction port spaced from the distal end of the probe. The probe comprises (A) an elongate shaft having a distal end portion with a longitudinal axis and (B) a probe head that is enlarged to extend laterally or transversely in two opposed directions relative to the shaft and the axis, the head having a recess or cavity facing laterally in a third direction relative to the shaft and the axis. The recess or cavity is defined in part by an inclined floor or base surface contiguous at a proximal end with the shaft and in part by a peripheral wall extending only partway around the recess or cavity, along a distal side and two lateral sides thereof. The cavity or recess is closed on a proximal side by the inclined surface and the shaft.

The at least one sheath or sleeve is preferably exactly one sheath or sleeve. Optionally, the sheath or sleeve is longitudinally slidable relative to the probe to shift between a distal position and a proximal position.

The inclined floor or base surface of the probe cavity is planar or flat and the recess or cavity is further defined by an additional floor or base surface located distally of the inclined floor or base surface, the additional floor or base surface being planar or flat and oriented parallel to the axis.

The probe head is provided with a first opening or through hole in the floor of the recess or cavity, spaced from the peripheral wall. The probe head is provided with a second opening or through hole in the peripheral wall. The probe head may be provided in the floor of the recess or cavity with a groove. In that case, the first opening or through hole is located in the groove while the groove extends to the second opening or through hole.

The peripheral wall preferably includes a cylindrical section on the distal side of the recess or cavity and further includes two linear sections on the lateral sides of the recess or cavity, so that the peripheral wall has a U-shaped configuration.

The peripheral wall is preferably provided with a beveled surface, on a side of the peripheral wall opposite the recess or cavity, and has a flat terminal edge in a plane parallel to the axis. The bevel tapers the peripheral wall towards the flat terminal edge or rim.

Pressurized coolant liquid enters the recess or cavity in the probe head from the channel or bore in the instrument shaft and exits in part through the openings in the floor or base and the semi-cylindrical portion of the peripheral wall. The diameters of the channel and the openings in the probe head, as well as the pressure of the fluid and the magnitude of applied suction must be taken into account in optimizing the rate of coolant flow so that the entire probe head is maintained within a desirable temperature range.

A surgical method in accordance with the present invention utilizes an ultrasonic surgical probe comprising an elongate shaft having a distal end portion with a longitudinal axis and further comprising a probe head that is enlarged to extend laterally or transversely in two opposed directions relative to the shaft and the axis. The head has a recess or cavity facing laterally in a third direction relative to the shaft and the axis, and the recess or cavity is defined in part by an inclined floor or base surface contiguous at a proximal end with the shaft. The recess or cavity is also defined in part by a peripheral wall extending only partway around the recess or cavity, along a distal side and two lateral sides thereof, the cavity or recess being closed on a proximal side by the inclined surface and the shaft. The method comprises manipulating the probe to press the head and particularly at least a portion of the peripheral wall into tissue at a surgical site. While continuing to press the head and the portion of the peripheral wall into the tissue, one draws the probe and concomitantly the portion of the peripheral wall in a proximal direction across the tissue, substantially (mostly) parallel to the surgical site. During that drawing process, ultrasonic vibrations are conducted into the probe. Tissue is separated from the surgical site by the drawing of the probe and the ultrasonic vibrating thereof. Upon the separating of the tissue, the separated tissue is deflected or moved out of the recess or cavity in part by contact of the separated tissue with the inclined floor or base surface. During the drawing of the probe, an irrigation liquid is fed to the recess or cavity via a longitudinal channel or bore in the probe shaft. The irrigation liquid serves to cool the probe head and assists in moving the separated tissue out of the recess or cavity. Flow of the liquid irrigant/coolant is maintained in part where the probe head is formed with at least one opening or through hole through which the liquid is aspirated into a surrounding sheath or sleeve. The cross-sectional areas of the channel or bore and the opening(s) in the probe head, as well as the pressure f liquid feed and the degree of suction are selected in concert to ensure adequate cooling of the probe head.

BRIEF DESCRIPTION OF THE DRAWINGS

FIG. 2 is a schematic right side, top and front perspective view of the device of FIG. 1.

FIG. 3 is an exploded right side, top and front perspective view of a probe and sheath included in the device of FIGS. 1 and 2.

FIG. 4 is an exploded left side, top, and rear perspective view of the probe and sheath of FIGS. 1-3.

FIG. 5 is a rear elevational view of the probe and sheath of FIGS. 1-4.

FIG. 7 is a top plan view of an ultrasonic surgical probe in accordance with the present invention.

FIG. 8 is a front end elevational view of the probe of FIG. 7.

FIG. 9 is a right side elevational view of the probe of FIGS. 7 and 8.

FIG. 10 is a right, top and rear isometric view of a head of the probe of FIGS. 7-9.

FIG. 11 is a right, bottom and front isometric view of the probe head of FIG. 10.

FIG. 12 is a right, top and front isometric view of the probe head of FIGS. 10 and 11.

FIG. 13 is a top, front and let side isometric view of the probe head of FIGS. 10-12.

DETAILED DESCRIPTION

Figure 1:
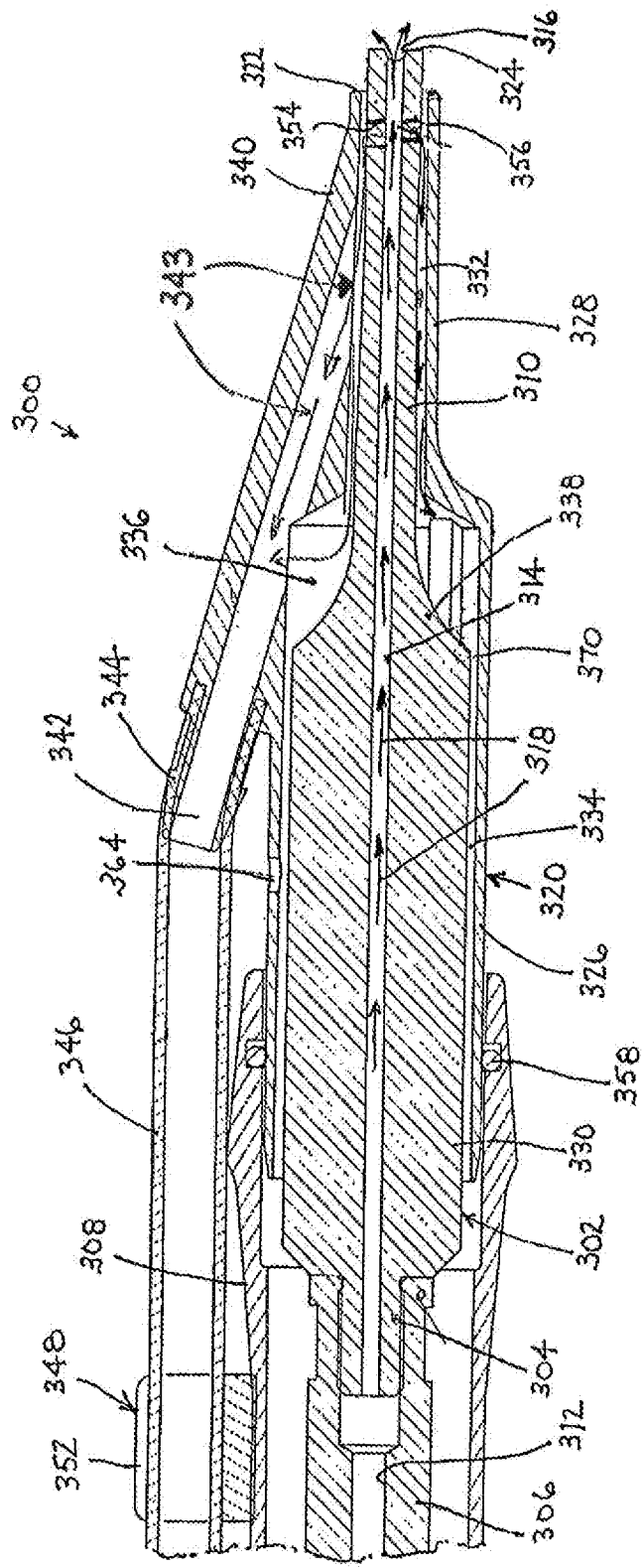
FIG. 1 is a partial longitudinal cross-sectional view of a device for debriding or removing biofilm from a wound site.
Figure 6:
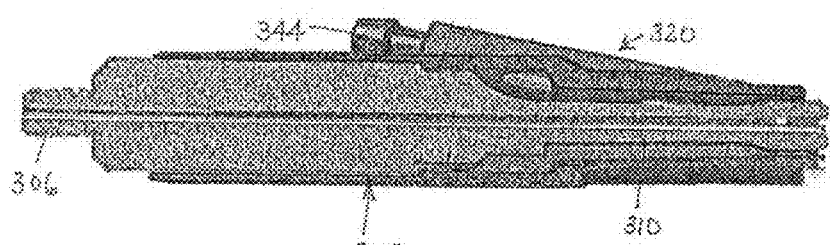
FIG. 6 is a partial cross-sectional view, similar to FIG. 1, taken along line VI-VI in FIG. 5.

As depicted in FIGS. 1-6, a surgical device 300 for debriding or removing tissue and biofilm from a wound site comprises an ultrasonic probe 302 which is attached at a proximal end via threaded connector 304 to a driver 306 is operatively connected to a generator of vibratory energy, typically a piezoelectric transducer array (not shown). Both the driver 306 and the piezoelectric transducer are located in a handpiece which has a cover or housing (not shown) connected to a casing 308. Probe 302 tapers down on a distal side to a distal end section 310. It is to be noted that the terms "horn" and "probe" are used synonymously.

Driver 306 and probe 302 are formed with mutually aligned axial channels or bores 312 and 314 that define a lumen (not separately designated) for the delivery of irrigant to a distal end aperture 316 in probe horn section 310, as indicated by flow arrows 318.

Surgical device 300 further includes a rigid sheath 320 that is shiftably mounted to casing 308 to vary a position of a distal tip 322 of the sheath relative to a distal tip or end face 324 of probe 302. Sheath 320 includes a cylindrical rear section 326 and a rectangularly prismatic forward section 328, which correspond geometrically to cross-sections of horn 310 and a proximal portion 330 of probe, 302, respectively.

Together with an outer surface (not designated) of probe horn 310, forward sheath section 328 defines a forward or distal channel or conduit 332, which is rectangular in cross-section. Together with an outer surface (not designated) of proximal probe portion 330, rear sheath section 326 defines a rearward or proximal channel or conduit 334, which is circular in cross-section. At a distal end, rearward channel 334 expands to an enlarged space 336 owing to the tapering of the probe at 338.

Sheath 320 is provided with an arm 340 that is connected at a forward or distal end to forward section 326 and is angled outwardly at a proximal side. Sheath arm 340 includes a main aspiration channel 342 that communicates at a distal end with forward channel 332. At a more proximal location, aspiration channel 342 of arm 340 communicates with rearward channel 334 and more particularly with enlarged space 336. At a proximal end, arm 340 is provided with an undercut connector port 344 which receives a resilient aspiration tube 346 in a friction fit. Aspiration tube 346 is fastened to casing 308 via a pair of clips 348 each formed with a pair of slotted annular rings 350 and 352 for receiving casing 308 and aspiration tube 346, respectively.

At a forward or distal end, probe horn 310 is formed with one or more apertures or cross-bores 354 and 356 that communicate on an inner side with channel or lumen 314 and on an outer side with forward channel 332. At a rear end, rear section 326 of sheath 320 is inserted between proximal probe portion 330 and a distal end of casing 308. An O-ring seal 358 is provided between casing 308 and an outer surface of sheath rear section 326.

A distal end of horn section 310 is formed into a probe head 360 that is extended in a traverse dimension, orthogonally to a longitudinal axis of the probe 302. Head 360 may particularly take a form disclosed in U.S. patent application Ser. No. 14/172,566, Publication No. 2015/0216549, the disclosure of which is incorporated by reference herein. In particular, head 360 includes a plurality of teeth 362 arranged in two mutually parallel rows along opposing edges or sides of the distal end face 324 of the probe head.

As indicated above, sheath 320 is slidable or longitudinally shiftable relative to probe 302 so as to be continuously adjustable as to axial or longitudinal position relative to probe head 360 anywhere from a fully extended position, where the distal tip 322 of sheath 320 is essentially coplanar with the distal end face 324 of probe head 360, to a retracted position where at least the teeth 362 of probe head 360 are fully exposed. O-ring 358 enables the adjustable positioning of sheath 320.

Apertures or cross-bores 354 and 356 serves as bypass holes, regardless of the relative longitudinal positioning of sheath 320 and probe 302. A vacuum under-pressure applied to the internal spaces of sheath 320, i.e., aspiration channel 342 (directional arrows 343 representing suction and irrigation flow), forward channel 332, and rearward channel 334, by a suction source (not shown) enables the capturing and removal of most of the irrigant that is delivered through central channel 314 (flow arrows 318). Accumulation of irrigant within sheath 320, especially when the device is used in a predominantly vertical orientation, is prevented by the provision of two suction pathways, namely, between aspiration channel 342 and each of the forward channel 332 and rearward channel 334. Irrigant not captured via a distal pathway is captured in a proximal pathway.

Where tissue fragments are small enough to be aspirated through the gap between the probe 302 and the sheath 320, clogging is prevented by designing the aspiration pathway of channel 324 to gradually increase in cross-sectional area from the probe-sheath gap at the distal end of the instrument all the way to the aspiration line. A vent port 364 may be provided in the rear sheath section 326 to reduce the magnitude of vacuum-generated pull force acting on the tissue which is driven towards and into the probe-sheath gap during debridement.

Matching or cooperating features 366 and 368 are respectively disposed on the outer side of the probe 302 and the inside of rear sheath section 326, in close proximity to a nodal plane or the probe, to facilitate probe-sheath alignment. This minimizes the chances of a probe-sheath contact at the points of maximum vibratory motion (antinodes), particularly at end face 324 of probe head 360. Due to their placement at a location of minimal vibratory displacement, e.g., the junction 370 between cylindrical probe portion 330 and tapering probe section 338, the alignment features 366 and 368 allow for the probe-sheath contact necessary for preventing or minimizing the unwanted interaction in the area of maximum vibratory displacement.

FIGS. 7-13 depict an ultrasonic surgical probe 102 that may be used instead of probe 302 for debriding tissue or removing biofilm from a wound site. Probe 102 comprises an elongate shaft 104 having an enlarged proximal end portion 106 with a screw-type coupling 108 for connection to a source of ultrasonic mechanical vibratory energy. Shaft 104 has a distal end portion 110 with a longitudinal axis 112 and a probe head 114 that is enlarged to extend laterally or transversely in two opposed directions (arrows 116, 118) relative to shaft 104 and axis 112. Head 114 is formed with a recess or cavity 120 facing laterally in a third direction (arrow 122) relative to shaft 104 and axis 112. Where head 114 may be seen as lying in a plane defined by axis 112 and extension directions 116 and 118, recess or cavity 120 faces in direction 122 perpendicular to that plane. Recess or cavity 120 is defined in part by an inclined floor or base surface 124 contiguous at a proximal end with shaft 104. Recess or cavity 120 is further defined in part by a peripheral wall 126 extending only partway around the recess or cavity, with a cylindrical wall portion 128 along a distal side of head 114 and two linear or planar wall sections 130, 132 along lateral sides thereof. Peripheral wall 126 thus has a U-shaped plan or configuration. Recess or cavity 120 is closed on a proximal side by inclined surface 124 and shaft 104.

Recess or cavity 120 is further defined by an additional floor or base surface 134 located distally of inclined floor or base surface 124. Additional floor or base surface 134 is planar or flat and oriented parallel to shaft axis 112. Preferably, inclined floor or base surface 124 is also planar or flat. Floor or base surfaces 124 and 134 are preferably adjacent and contiguous with one another.

Probe head 114 is provided in at least one opening 136 in either inclined floor surface 124 and/or parallel floor surface 134. Opening 136 is spaced from the peripheral wall 126. Opening 136 permits the egress of pressurized fluid from recess or cavity 120 into a space surrounding probe head 114, exemplarily into a channel 138 in a sheath 140 that surrounds the probe 102 (see discussion above with reference to cross-bores 354 and 356 shown in FIG. 1 and description hereinbelow with reference to FIGS. 14 et seq.). The pressurized fluid is a liquid irrigant for cooling the surfaces of the probe head 120 particularly including surfaces of peripheral wall 126 and other surfaces that contact tissue at a surgical site during an ultrasonic debridement or biofilm removal procedure. The pressurized fluid is fed into recess or cavity 120 via an axial channel or through bore 142 in probe shaft 104. Channel or through bore 142 has an outlet port 144 at least partially in or at inclined floor or base surface 124.

Preferably, probe head 114 is provided with a further opening or through hole 146 in peripheral wall 126 at a distal end of the probe head, particularly in cylindrical wall section 128. A groove 148 is formed in floor surfaces 124 and 134 of recess or cavity 120, with opening or through hole 136 located in the groove, the groove extending to cylindrical wall section 128 and particularly to opening or through hole 146 therein.

Groove 148 is typically formed during manufacture during a drilling of a probe blank (not separately shown) to form channel or bore 142 in probe shaft 104. Inclined floor or base surface 124 and the distal floor or base surface 134 are subsequently formed by machining one side of the head of the blank. This machining opens a side of the channel in the head and thereby generates groove 148.

Peripheral wall 126 is provided with a beveled surface 150, on a side of the peripheral wall opposite recess or cavity 120, and has a flat terminal edge 152 in a plane parallel to axis 112 and the plane of head 114. The flat terminal edge or rim 152 enables the peripheral wall 126 to transmit ultrasonic vibratory energy into the tissues at a surgical site during a debridement or biofilm elimination procedure.

It is to be noted that the multiple openings 136, 146 in the probe head 114, one in the floor 124, 134 and one in on the distal portion 128 of peripheral wall 126, facilitate the flow of liquid irrigant in part to optimize cooling of the peripheral wall and the tissues at the surgical site, thus reducing if not eliminating damage to the healthy tissue which remains after the debridement procedure.

The floor geometry of recess or cavity 120 in probe head 114 acts to deflect and guide removed tissue fragments from the recess or cavity, thereby inhibiting if not completely preventing the clogging of the openings 136, 146 in the probe head. In addition, the flow of liquid irrigant or coolant into the recess or cavity 120 through the channel or bore 142 in shaft 104 and out through the openings 136, 146 in the floor 124, 134 and the peripheral wall 126 help move the separated tissue fragments along the floor surfaces 134, 124 and out of the recess or cavity 120. The floor structure of recess or cavity 120 assists in maintaining desired cooling for longer periods of time.

Figure 14:
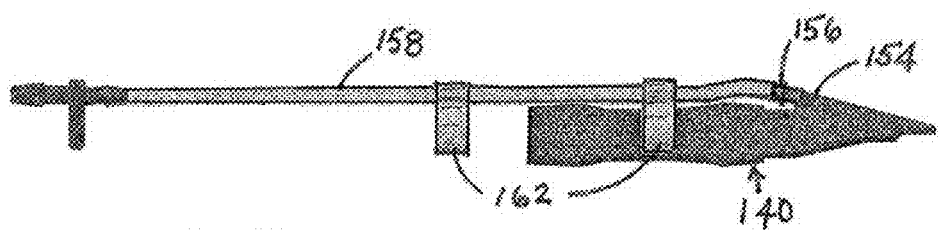
FIG. 14 is a side elevational view of a sheath for an ultrasonic surgical instrument assembly in accordance with the present invention.
Figure 15:
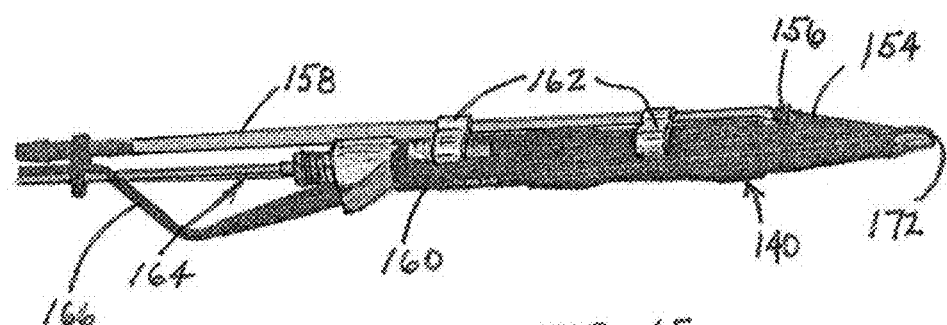
FIG. 15 is a bottom, and right side isometric view of an instrument assembly including the sheath of FIG. 14 and the probe of FIGS. 7-13.
Figure 16:
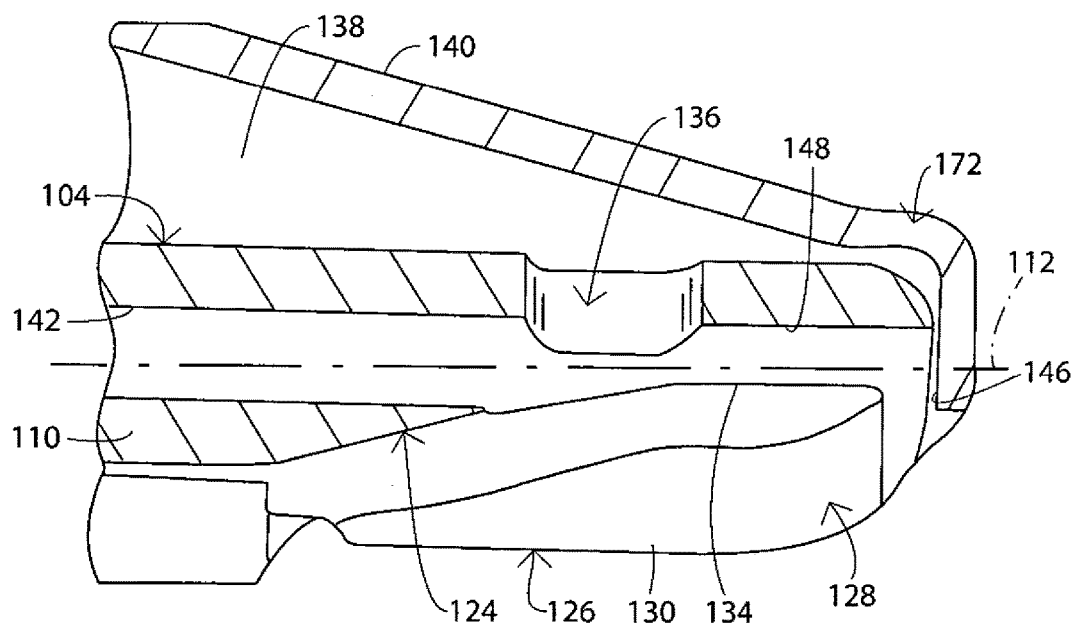
FIG. 16 is a schematic and diagrammatic longitudinal cross-sectional view, on an enlarged scale, of a distal end portion of the instrument assembly of FIGS. 14 and 15.

FIGS. 14-19 depict a surgical instrument assembly incorporating probe 102 and including sheath or sleeve 140 disposed about probe 102. As shown in FIGS. 14 and 15, sheath 140 includes an eccentric suction arm 154 extending at an angle away from a distal end of the sheath. A connector 156 provided at a proximal end of the suction arm 154 is force-fit into a distal end of a length of vacuum tubing 158 that is further attached to the sheath 140, as well as to a transducer housing 160 via a plurality of spring clips 162. FIG. 15 also shows a liquid conduit 164 coaxial with probe axis 112 and an electrical cable 166 that provides an ultrasonic-frequency power signal to the transducer disposed inside housing or handpiece 160.

As described hereinabove with reference to FIGS. 1-6, sheath or sleeve 140 defines at least a first suction port 168 at a distal end of the probe, proximate the operative tip or head 114 thereof, and a second suction port 170 (FIG. 18) spaced back from the distal end of the probe. The relationship between probe 102 and sheath or sleeve 140 is analogous to that described above with reference to FIGS. 1-6.

Sheath or sleeve 140 is preferably exactly one sheath or sleeve longitudinally slidable relative to probe 102 to shift between a distal position and a proximal position. Sheath or sleeve 140 has a distal end wall section 172 that is disposed transversely or perpendicularly to the probe axis 112 (which is co-linear or co-incident with an axis of sheath 140). Distal end wall section 172 facilitates collection and extraction of liquid irrigant that exits probe head 114 and more particularly cavity or recess 120 via opening or through hole 146 in cylindrical section 128 of peripheral wall 126. The purpose of irrigant collection and extraction is two-fold: to prevent the irrigant from overflowing a surgical site and the operating table and to facilitate temperature control.

Figure 17:
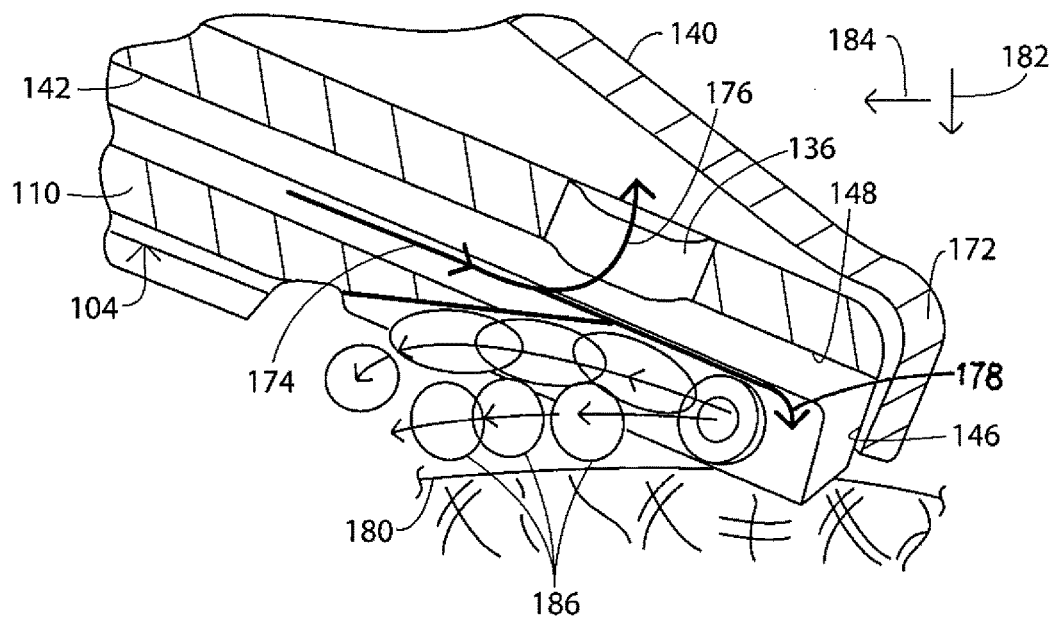
FIG. 17 is a schematic and diagrammatic longitudinal cross-sectional view similar to FIG. 16, showing use of the instrument assembly in debriding or removing tissue and biofilm from a wound site, with directional arrows indicating tissue fragment transport.
Figure 18:
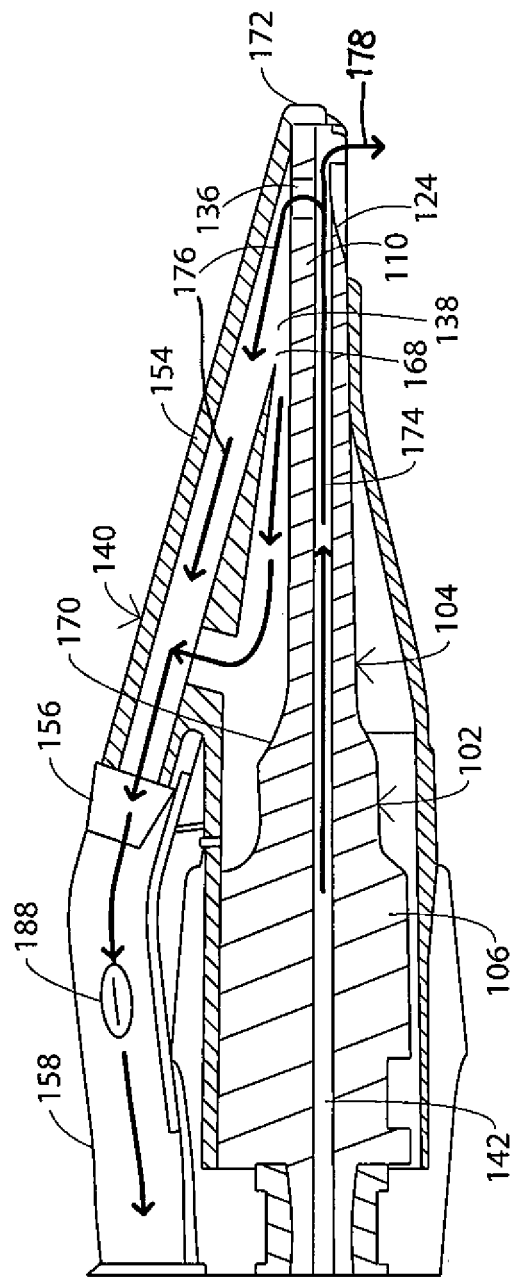
FIG. 18 is a schematic and diagrammatic longitudinal cross-sectional view, on a smaller scale, showing a larger distal end portion of the instrument assembly of FIGS. 14 and 15 than visible in FIGS. 16 and 17 and with directional arrows indicating flow of liquid coolant or irrigant.
Figure 19:
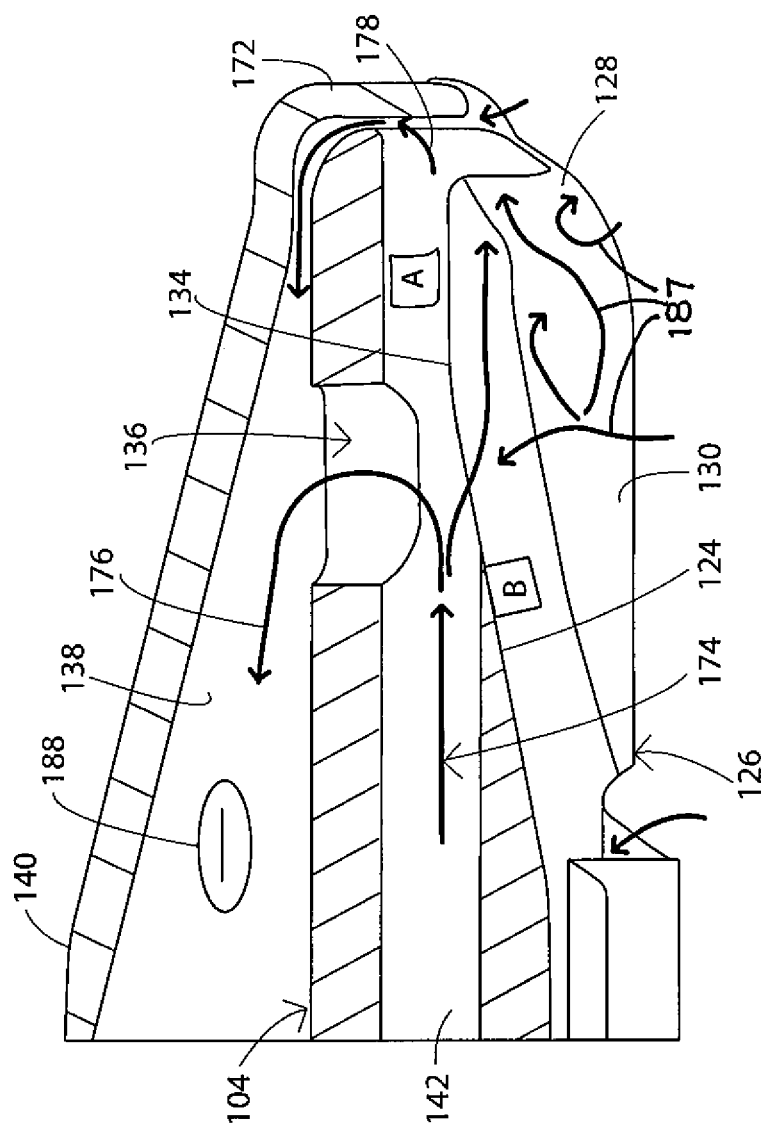
FIG. 19 is a schematic and diagrammatic longitudinal cross-sectional view identical to FIG. 16, with directional arrows to represent irrigation liquid flow paths.

Pressurized coolant liquid enters recess or cavity 120 in probe head 114 from channel or bore 142 in instrument shaft 104, as indicated by arrows 174 in FIGS. 17-19, and exits in part through opening 136 in floor or base surface 124 or 134, as represented by arrows 176, and opening 146 in semi-cylindrical portion 128 of peripheral wall 126 (arrows 178). Some of the irrigant that enters recess or cavity 120 from channel or bore 142 forms a slurry with tissue fragments that are removed from a surgical site 180 (FIG. 17) during a debridement or biofilm-removal procedure in which the ultrasonically vibrating probe head 114 and particularly rim or surface 152 thereof is pressed into the tissue, as indicated by a first force arrow 182 (FIG. 17), and then dragged in a proximal direction as represented by a second force arrow 184. In this operation, the slurry of irrigant and tissue fragments moves in circular flow patterns 186 guided by inclined floor or base surface 124 of probe head 114. The tissue fragments are thus deflected out of the cavity 120 and away from openings 136 and 146, thereby delaying if not preventing clogging of the openings and the suction path inside eccentric suction arm 154 of sheath 140. The diameters or cross-sectional areas of channel or bore 142 and of openings 136 and 146 in probe head 114, as well as the pressure of the fluid (174) and the magnitude of applied suction (negative-sign symbols 188) must be taken into account in optimizing the rate of coolant flow so that the entire probe head 114 is maintained within a desirable temperature range.

During the pressing (182) and drawing (184) of probe 144 during a debridement or biofilm-removal procedure, irrigation liquid or coolant is fed to recess or cavity 120 via channel or bore 142 in probe shaft 104. The irrigation liquid serves to cool the probe head 114 and assists in moving the separated tissue via slurry flow 186 out of recess or cavity 120. Flow of the liquid irrigant/coolant (directional arrows 187 representing irrigation liquid flow paths in FIG. 19) is maintained in part by openings or through holes 136, 146 through which the liquid is aspirated into sheath or sleeve 140.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic surgical probe comprising:
   an elongate shaft having a distal end portion with a longitudinal axis; and
   a probe head that is enlarged to extend laterally or transversely in two opposed directions relative to said shaft and said axis,
   said head having a recess or cavity facing laterally in a third direction orthogonal or transverse to said shaft and said axis,
   said recess or cavity being defined in part by an inclined floor or base surface contiguous at a proximal end with said shaft, said recess or cavity being further defined by an additional floor or base surface located distally of said inclined floor or base surface, said additional floor or base surface being planar or flat and oriented parallel to said axis,
   said recess or cavity being further defined in part by a peripheral wall extending only partway around said recess or cavity, along a distal side and two lateral sides thereof,
   said cavity or recess being closed on a proximal side by said inclined surface and said shaft.

2. The surgical probe defined in claim 1 wherein said inclined floor or base surface is planar or flat.

3. The surgical probe defined in claim 2 wherein said additional floor or base surface and said inclined floor or base surface are adjacent and contiguous with one another.

4. The surgical probe defined in claim 1 wherein said probe head has at least one opening or through hole in at least one of said inclined floor or base surface and said additional floor or base surface, said opening or through hole communicating with said recess or cavity.

5. The surgical probe defined in claim 4 wherein said opening or through hole is a first opening or through hole and is spaced from said peripheral wall, said probe head being provided with a second opening or through hole in a distal end portion of said peripheral wall.

6. The surgical probe defined in claim 5 wherein said probe head is provided in said cavity with a groove, said first opening or through hole being located in said groove, said groove extending along said additional floor or base surface to said second opening or through hole.

7. The surgical probe defined in claim 6 wherein said shaft is provided with an axial channel or through bore, said groove being continuous and coaxial with said channel or through bore.

8. The surgical probe defined in claim 4 wherein said shaft is provided with an axial channel or through bore having an outlet or opening into said recess or cavity.

9. The surgical probe defined in claim 1 wherein said peripheral wall includes a cylindrical section on said distal side of said recess or cavity.

10. The surgical probe defined in claim 9 wherein said peripheral wall further includes two linear sections on said lateral sides of said recess or cavity, said peripheral wall having a U-shaped plan.

11. The surgical probe defined in claim 10 wherein said peripheral wall is provided with a beveled surface, on a side of said peripheral wall opposite said recess or cavity, and has a flat terminal edge in a plane parallel to said axis.

12. A surgical instrument assembly comprising:
    an ultrasonic probe having an operative tip;
    an electromechanical transducer operatively connected to said probe for generating an ultrasonic standing wave in said probe; and
    at least one sheath or sleeve disposed about said probe and defining at least a first suction port at a distal end of said probe, proximate said operative tip, and a second suction port spaced from said distal end of said probe, wherein said probe comprises:

an elongate shaft having a distal end portion with a longitudinal axis; and a probe head that is enlarged to extend laterally or transversely in two opposed directions relative to said shaft and said axis, said head having a recess or cavity facing laterally in a third direction relative to said shaft and said axis, said recess or cavity being defined in part by an inclined planar or flat floor or base surface contiguous at a proximal end with said shaft, said recess or cavity being defined in part by a peripheral wall extending only partway around said recess or cavity, along a distal side and two lateral sides thereof, said cavity or recess being closed on a proximal side by said inclined surface and said shaft.

13. The surgical instrument assembly defined in claim 12 wherein said recess or cavity is further defined by an additional floor or base surface located distally of said inclined floor or base surface, said additional floor or base surface being planar or flat and oriented parallel to said axis.

14. The surgical instrument assembly defined in claim 13 wherein said probe head is provided in at least one of said inclined floor or base surface and said additional floor or base surface with a first opening or through hole communicating with said recess or cavity, said first opening or through hole being spaced from said peripheral wall, said probe head being provided with a second opening or through hole in said peripheral wall.

15. The surgical instrument assembly defined in claim 12 wherein said peripheral wall includes a cylindrical section on said distal side of said recess or cavity, said peripheral wall further including two linear sections on said lateral sides of said recess or cavity, said peripheral wall having a U-shaped plan.

16. The surgical instrument assembly defined in claim 15 wherein said peripheral wall is provided with a beveled surface, on a side of said peripheral wall opposite said recess or cavity, and has a flat terminal edge in a plane parallel to said axis.

17. The surgical instrument assembly defined in claim 12 wherein said first suction port and said second suction port are different openings in said at least one sheath or sleeve.

\* \* \* \* \*